United States Patent [19]
Chopdekar et al.

[11] Patent Number: 5,599,846
[45] Date of Patent: Feb. 4, 1997

[54] PHENYLEPHRINE TANNATE COMPOSITIONS

[75] Inventors: Vilas M. Chopdekar, Edison; James R. Schleck, Somerset; Vernon A. Brown, Maplewood; Cheng Guo, Harrison, all of N.J.

[73] Assignee: Jame Fine Chemicals, Inc., Bound Brook, N.J.

[21] Appl. No.: 671,160

[22] Filed: Jun. 28, 1996

[51] Int. Cl.$^6$ .................................................. A61K 31/135
[52] U.S. Cl. ............................................................. 514/653
[58] Field of Search ............................................. 514/653

[56] References Cited

U.S. PATENT DOCUMENTS 4,601,714  7/1986  Burnhill .................................. 604/286

Primary Examiner—Phyllis G. Spivack
Attorney, Agent, or Firm—Jack Matalon

[57] ABSTRACT

Phenylephrine tannate compositions are disclosed wherein the phenylephrine tannate has a minimum purity level of at least 95%. The composition also contains a minor amount of water, but no significant quantities of organic compounds or solvents other than water are present. The phenylephrine tannate will have a density of at least 0.6 g/cc.

6 Claims, No Drawings

PHENYLEPHRINE TANNATE COMPOSITIONS

FIELD OF INVENTION

The invention relates to phenylephrine tannate compositions. These compositions comprise phenylephrine tannate having a minimum purity level of at least 95 wt. %, based on the weight of the composition, together with a minor amount of water.

BACKGROUND OF INVENTION

Phenylephrine tannate compositions are well known and are widely used as antihistamines alone or in combination with other antihistamines such as chlorpheniramine tannate and pyrilamine tannate. Phenylephrine as the free base has a melting point of 169°–172° C. and may be prepared from m-hydroxy-ω-chloroacetophenone and methylamine, see U.S. Pat. Nos. 1,932,947 and 1,954,389.

Tannic acid, also known as tannin, is a well known naturally occurring substance. Commercially available tannic acid usually contains about 5 wt. % water, has a molecular weight of about 1700 and is typically produced from Turkish or Chinese nutgall.

Commercially available phenylephrine tannate compositions are relatively impure. Such compositions are prepared by reacting the phenylephrine free base with tannic acid in the presence of a volatile solvent, typically isopropanol. The yield is only fair (e.g. about 70%) and a significant amount of the volatile solvent, e.g. 6–10 wt. %, based on the weight of the composition, remains with the product and cannot be removed.

Typically, in the conventional isopropanol route, the phenylephrine free base and the tannic acid will be present in the isopropanol at a concentration of about 20 wt. %, based on the weight of the reaction mixture.

The reaction mixture is stirred for about one hour, while maintaining a temperature of 60°–70° C. The reaction mixture is cooled to room temperature and filtered. The precipitate is vacuum-dried for an extended period of time at a temperature of 60°–80° C. A yield of product of only about 70 % is obtained and the product purity will only be about 90 wt. % at best (the impurities will consist of isopropanol and degradation products which cannot be removed); the density of the product will be about 0.45 g/cc.

Phenylephrine tannate is quite heat sensitive and it therefore undergoes decomposition quite readily upon prolonged exposures to temperatures as low as 50° C. Accordingly, even when the solvent utilized in its preparation has a relatively high vapor pressure such as is in the case of isopropanol, it is impossible to reduce the solvent content below about 6 wt. %, based on the weight of the phenylephrine composition, even at reduced pressures and very mild elevated temperatures. Moreover, from an environmental point, it would be most desirable if phenylephrine tannate could be prepared such that the use of volatile solvents could be avoided.

SUMMARY OF INVENTION

It has now been found that it is possible to prepare very pure phenylephrine tannate by a synthetic route which results in the production of phenylephrine tannate having a minimum purity level of at least 95 wt. %, preferably at least 97 wt. %, based on the weight of the composition, with a yield of at least about 95%. The chief "impurity" present in the composition is water which is present in an amount of 1–5 wt. %, based on the weight of the composition. Indeed, it has been found possible to produce phenylephrine tannate having a purity level of at least 99 wt. % and a water content of less than 1 wt. %, based on the weight of the composition.

Since the pure phenylephrine tannate composition of the invention is administered either in solid form, i.e. a pill, or as a suspension, the minimal amount of water present in the composition cannot be considered to be an impurity of the nature associated with degradation products or volatile organic compounds such as isopropanol. The dosage to be administered can be readily adjusted by taking into account the insignificant amount of water present in the composition.

DETAILS OF THE INVENTION

The phenylephrine tannate compositions of the present invention are characterized as having a minimum purity of at least 95 wt. %, preferably a minimum purity of at least 97 wt. %, based on the weight of the composition. The amount of any organic compounds or solvents other than water present in the compositions of the invention, is less than about 1 wt. %, based on the weight of the composition.

Water will be present in the phenylephrine tannate compositions of the invention to a maximum extent of about 5 wt. %, preferably less than 3 wt. %, based on the weight of the composition. Indeed, when prepared in accordance with the process described below, it is generally possible to prepare compositions wherein the phenylephrine tannate will have a purity level of at least 99 wt. %, based on the weight of the composition, with the balance being water and no other organic compounds present as determined by HPLC analysis.

The phenylephrine tannate compositions of the invention will have a density of at least about 0.6 g/cc, preferably 0.7 to 0.9 g/cc. Such results are in sharp contrast to prior art phenylephrine tannate compositions in which the density is 0.4–0.5 g/cc and the maximum purity is about 85–90 wt. %, based on the weight of the composition, with the balance consisting of decomposition products and isopropanol.

The phenylephrine tannate compositions of the invention are prepared by a novel synthetic route. The phenylephrine in the form of its free base is contacted with tannic acid in the presence of water by stirring at a temperature of 20°–80° C. for a period of time ranging from minutes to one hour. In the event that the phenylephrine is present as the salt, e.g. the hydrochloride, it is dissolved in cold water and neutralized with a stoichiometric amount of a base such as sodium or potassium hydroxide. The phenylephrine free base precipitates out, recovered by filtration, washed with cold water until all chloride salts have been removed and air dried at ambient temperatures.

The molar ratio of phenylephrine free base to tannic acid will generally be stoichiometric, i.e. 5:1, although such ratio may vary somewhat since tannic acid is a complex substance which varies from batch to batch. The exact molar ratio to be used for a given batch of tannic acid may be readily determined by one skilled in the art by preparing small aliquot samples having slight variations on both sides of the 5:1 molar ratio and determining the exact molar ratio to be used after working up the product such that neither excess phenylephrine free base nor excess tannic acid will be present in the final product.

The amount of water to be used as the reaction diluent is not critical; 10–90 wt. % water, based on the weight of the entire reaction mixture may be used. Conveniently, the tannic acid will be present in the reaction vessel diluted with water to a concentration of 40–60 wt. %. Thereafter, the phenylephrine free base in solid form or as a suspension in water, e.g. 30–60 wt. % suspension, is slowly added to the reaction vessel, while stirring.

In order to avoid decomposition products from forming during the course of the reaction, it is desirable that the reaction be carried out at ambient temperatures, i.e. 0°–30° C. After completion of the reaction, the reaction mixture will develop two layers upon standing.

The water is removed from the reaction mixture by subjecting the entire reaction mixture to freeze-drying, a well known technique for removing water from compositions. Although freeze-drying to remove the water is a time-consuming process (one liter of reaction mixture containing one liter of water will typically take 30–36 hours to remove about 97 wt. % of the water present in the reaction mixture), it has been found to be the only method for removing water from the heat-sensitive phenylephrine tannate without any significant formation of decomposition products. While volatile organic solvents such as isopropanol may be more quickly removed by evaporation at reduced pressures and elevated temperatures, there will always be impurities, i.e. isopropanol and decomposition products, in the product which cannot be removed without further degradation of the product. Moreover, as mentioned above, the water route coupled with freeze-drying to remove the water will result in a yield of at least about 95%, versus the typical yield of about 70% obtained from the isopropanol route.

Typically, the freeze-drying is carried out at a pressure of not greater than about 500 milliTorre and a temperature of about −60° to −20° C. Preferably, the freeze-drying is carried out at a pressure in the range of 300 to 100 milliTorre and a temperature in the range of −50° to −40° C. The desired end point of the freeze-drying process may be determined by condensing and measuring the quantity of water vapor removed during the freeze-drying process. The time required for completion of the freeze-drying process will vary depending on factors such as pressure, temperature, quantity to be freeze-dried, desired level of water to be tolerated in the final product, the thickness and surface area of the reaction mixture layers in the trays of the freeze-drying equipment, etc.

The following nonlimiting examples will serve to illustrate the present invention.

EXAMPLE 1 (COMPARATIVE EXAMPLE)

In this example, phenylephrine tannate was synthesized by the isopropanol route for comparative purposes. A reaction vessel consisting of a 2-liter, 3-neck flask was set up with a thermometer, stirrer, condenser and heating mantle. 20 g phenylephrine free base and 400 g isopropanol were added to the flask and the contents were heated, with stirring, to 65°–70° C. in order to dissolve the phenylephrine base. A separate solution of 43.2 g of tannic acid (mol. wt. of about 1700) in 400 g isopropanol was prepared and heated to 40° C., with stirring.

The tannic acid solution was slowly added, with stirring, to the reaction vessel over a period of about 30 minutes, while maintaining the contents of the reaction vessel at a temperature of about 70° C. The reaction mixture was stirred for about 60 minutes, while maintaining a temperature of about 70° C. and was thereafter cooled to about 15° C. The phenylephrine tannate product was recovered from the reaction mixture by filtration and was then washed with 50 g of isopropanol.

The phenylephrine product was then vacuum dried at about 1 mm Hg pressure and at about 60° C. temperature over a period of about 60 minutes. The yield of product was 45.5 g (72% yield) and its density was 0.4 g/cc. GC and HPLC analysis indicated that the product contained about 8 wt. % isopropanol and about 2 wt. % of degradation products. All efforts to remove the isopropanol and degradation products by further prolonged vacuum drying failed.

EXAMPLE 2

Phenylephrine tannate was synthesized by the water route as follows. In a 5-liter flask were placed 680 g tannic acid (mol. wt. of about 1700) in 1 kg water. The temperature of the solution was ambient (about 22° C.) and, while stirring, 320 g phenylephrine free base were added to the flask over a 15-minute period. Stirring was continued for an additional 2 hours. Upon allowing the reaction mixture to stand, it was noted that two layers had formed.

The entire mass of the reaction mixture was then freeze-dried at a reduced pressure of 200–100 milliTorre and a temperature of −50° to −40° C. for about 36 hours. At this point, the water which had been removed was condensed and its weight equalled about 1 kg. The dried phenylephrine tannate was found to contain 2 wt. % of water and it had a density of 0.8 g/cc. Analysis of the product by HPLC showed no discernible amounts of materials other than phenylephrine tannate and water. The overall yield of product was 96%.

What is claimed is:

1. A composition comprising:
   (a) phenylephrine tannate having a minimum purity level of at least about 95 wt %, based on the weight of the composition; and
   (b) water.

2. The composition of claim 1 wherein the minimum purity level is at least 97 wt. %, based on the weight of the composition.

3. The composition of claim 1 wherein the water is present at a maximum level of about 5 wt. %, based on the weight of the composition.

4. The composition of claim 3, wherein the water is present at a maximum level of 3 wt. %, based on the weight of the composition.

5. The composition of claim 1 wherein the phenylephrine tannate has a density of at least about 0.6 g/cc.

6. The composition of claim 5 wherein the density is in the range of 0.7 to 0.9 g/cc.

* * * * *